United States Patent [19]

Weis et al.

[11] Patent Number: 4,663,290

[45] Date of Patent: May 5, 1987

[54] PRODUCTION OF REVERSE TRANSCRIPTASE

[75] Inventors: John H. Weis, Minneapolis; John S. Salstrom, Edina, both of Minn.

[73] Assignee: Molecular Genetics, Inc., Minnetonka, Minn.

[21] Appl. No.: 341,321

[22] Filed: Jan. 21, 1982

[51] Int. Cl.$^4$ .................. C12N 1/20; C12N 9/00; C12N 15/00; C12N 1/00; C12N 9/10; C12P 21/00; C12P 19/34

[52] U.S. Cl. .................. 435/253; 435/68; 435/91; 435/18.3; 435/172.3; 435/317; 435/193; 935/14; 935/29; 935/73

[58] Field of Search .................. 435/68, 70, 91, 172, 435/253, 317, 183, 235, 172.3, 193; 536/27; 935/14, 29, 73

[56] References Cited

U.S. PATENT DOCUMENTS

| | | | |
|---|---|---|---|
| 4,332,892 | 6/1982 | Ptashne et al. | 435/68 |
| 4,338,397 | 7/1982 | Gilbert et al. | 435/68 |
| 4,356,270 | 10/1982 | Itakura | 435/68 |

OTHER PUBLICATIONS

Botstein et al., Recombinant DNA Technical Bulletin 2(2), 49 (1979).
*Genes*, Lewin, 1983, John Wiley & Sons, New York, pp. 13–15 and 584 and 684.
*Gene Expression*, vol. 3, Lewin, 1977, John Wiley & Sons, New York, pp. 13–15 and 296–297.
Roberts et al., "A General Method for Maximizing the Expression of a Cloned Gene", Proc. Natl. Acad. Sci. USA 76: 760 (1979).
Baltimore, 1970, Nature 226:1209.
Bolivar and Backman, 1979, Methods in Enzymology 68:245.
Chang et al., 1978, Nature 275:617.
Copeland et al., 1980, J. Virol. 36:115.
Fraser et al., 1978, Proc. Natl. Acad, Sci., U.S.A. 75:5936.
Gerard and Grandgenett, *Molecular Biology of RNA Tumor Viruses*, Ed. J. R. Stephenson, Academic Press, New York, N.Y., 1980.
Guarente et al., 1980, Cell 20:543.
Guerry et al., 1973, J. Bacteriol. 116:1063.
Guntaka et al., 1976, J. Mol. Biol. 106:337.
Highfield et al., 1980, J. Virol. 36:271.
Hizi, 1977, J. Biol. Chem. 252:2281.
Itakura et al., 1977, Science 198:1056.
Johnson, 1977, Biochemistry 16:4217.
Kacian et al., 1971, Biochim. Biophys. Acta 246:365.
Kelly et al., 1970, J. Biol. Chem. 245:39.
Kieras & Faras, 1975, Virology 65:514.
Laemmli, 19 Nature 227:680.
Maniatas et al., 1975, Proc. Natl. Acad. Sci., U.S.A. 72:1184.
Maxam and Gilbert, 1980, *Methods in Enzymology* 65:499.
Mercereau-Puijalon et al., 1978, Nature, 275:505.
Miller, *Experiments in Molecular Genetics*, Cold Spring Harbor Press, New York, N.Y. 1972, pp. 47–55, 221–229, 230–234, 352–355, 356–359, 431–435.
Seeburg et al., 1978, Nature 276:795.
Southern, 1975, J. Mol. Biol. 98:503.
Temin and Mizutani, 1970, Nature 226:1211.
U.S. Pat. No. 4,237,224, Cohen and Boyer.
U.S. Pat. No. 4,304,863, Collins and Hohn.
Verma, 1977, Biochem. Biophys. Acta 473:1.
Villa-Komaroff et al., 1978, Proc. Natl. Acad. Sci., U.S.A. 75:3727.
Hunter et al., Cold Spring Harbor RNA Tumor Virus Meeting (1981) May 20–24, p. 133.
Schwartz, 1981, Cold Spring Harbor RNA Tumor Virus Meeting, p. 13.

*Primary Examiner*—James Martinell
*Attorney, Agent, or Firm*—Pennie & Edmonds

[57] ABSTRACT

Methods are described for the production of the β-subunit of reverse transcriptase using recombinant DNA techniques. Methods and compositions are described for cloning and expressing the gene coding for the β-subunit of reverse transcriptase and characterizing and isolating the gene product. The recombinant plasmids constructed herein contain the necessary signals and controls for efficient expression of the reverse transcriptase gene in bacteria and other microorganisms. The isolated reverse transcriptase gene product is a functional, metabolically stable and biologically active protein.

5 Claims, 12 Drawing Figures

FIG. 1

```
START
*THR.VAL.ALA.LEU.HIS.LEU.ALA.ILE.PRO.LEU.LYS.TRP.LYS.PRO.ASP.
 ACT.GTT.GCG.CTA.CAT.CTG.GCT.ATT.CCG.CTC.AAA.TGG.AAG.CCA.XXC.

HIS.THR.PRO.VAL.TRP.ILE.PHE.GLN.TRP.PRO.LEU.PRO.GLU.GLY.LYS.
 CAC.ACG.CCT.GTG.TGG.ATT.TTC.CAG.TGG.CCC.CTC.CCT.GAA.GGC.AAA.

LEU.VAL.ALA.LEU.THR.GLN.LEU.VAL.GLU.LYS.GLU.LEU.GLN.LEU.GLY.
 CTT.GTA.GCG.CTA.ACG.CAA.TTA.GTC.GAA.AAA.GAA.TTA.CAG.TTA.GGA.

HIS.ILE.GLU.PRO.PRO.LEU.SER.CYS.TRP.ASN.THR.PRO.VAL.PHE.VAL.
 CAT.ATA.GAG.CCC.TCA.CTT.AGT.TGC.TGG.AAC.ACA.CCT.GTC.TTT.GTG.

ILE.ARG.LYS.ALA.SER.GLY.SER.TYR.ARG.LEU.LEU.HIS.ASP.LEU.ARG.
 AXC.CGG.AAG.GCT.TCC.GGG.TCG.TAT.CGC.TTA.TTG.CAT.GAT.TTG.CGC.

ALA.VAL.ASN.ALA......ALA.ALA.ASN.GLU.SER
 GCT.GTT.AAC.GCC......GCT.GCC.AAC.GAG.AGT*
                                        END
```

FIG. 3a

FIG. 3c

PRODUCTION OF REVERSE TRANSCRIPTASE

TABLE OF CONTENTS

1. Field of the Invention
2. Background of the Invention
   2.1 Recombinant DNA Technology
   2.2 Retroviruses
   2.3 Gene Expression
3. Summary of the Invention
4. Description of the Invention
   4.1 Identification and Isolation of the Reverse Transcriptase Gene
   4.2 Insertion of the Reverse Transcriptase Gene into a Cloning Vector
   4.3 Insertion of a Promoter Into the Cloning Vector
   4.4 Reconstruction of the Reverse Transcriptase Gene
   4.5 Purification of Reverse Transcriptase
5. Examples
   5.1 Identification of the Reverse Transcriptase Gene
   5.2 Isolation of the Reverse Transcriptase Gene
      5.2.1 Plasmid Isolation
      5.2.2 Isolation of the Reverse Transcriptase Gene from pRSV60
   5.3 Production of Fusion Gene
      5.3.1 Preparation of the pLG Plasmids
      5.3.2 Ligation of the Reverse Transcriptase Gene Fragment into pLG200, pLG300 and pLG400
   5.4 Construction of a Unique Restriction Site in the Cloning Vector
   5.5 Insertion of the Lac Promoter Into the Cloning Vector
      5.5.1 Progressive Digestion of pRT Linear DNA
      5.5.2 Lac Promoter Insertion
   5.6 Fusion Protein Assays
      5.6.1 Polypeptide Analysis
      5.6.2 Immunoassay
   5.7 Reconstruction of the Reverse Transcriptase Gene
   5.8 Identification of the Reverse Transcriptase Gene Product
      5.8.1 Preparing the Cell Lysate
      5.8.2 Immunoprecipitation
      5.8.3 Preparation for SDS-PAGE
   5.9 Purification of the Reverse Transcriptase Gene Product
   5.10 Characterization of the Reverse Transcriptase Gene Product

FIELD OF THE INVENTION

This invention relates to a process for the production of a viral protein, the β-subunit of the reverse transcriptase of Avian Sarcoma Virus (ASV), and to processes and compositions for making and using novel DNA sequences, plasmids and microorganisms to produce this viral protein. The present invention utilizes recombinant DNA techniques to insert the gene coding for the β-subunit of ASV-reverse transcriptase, or a portion thereof, into a DNA vector, such as viral DNA, plasmid DNA or bacteriophage DNA, such that the vector is capable of replicating and directing efficient expression of the reverse transcriptase gene in a bacterial host or other foreign single cell system. The resulting recombinant plasmid is used to transform host cells and thereby enable production of reverse transcriptase in the host cells.

2. BACKGROUND OF THE INVENTION

2.1 Recombinant DNA Technology

Recombinant DNA technology involves insertion of specific DNA sequences into a DNA vehicle (vector) to form a recombinant plasmid. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant plasmids. For example, U.S. Pat. No. 4,237,224 to Cohen and Boyer describes production of such plasmids using restriction enzymes and methods known as ligation. These recombinant plasmids are then introduced into unicellular organisms by means of transformation. Because of the general applicability of the techniques described therein, U.S. Pat. No. 4,237,224 is hereby incorporated by reference into the present specification.

Another method for introducing recombinant plasmids into unicellular organisms is described by Collins and Hohn in U.S. Pat No. 4,304,863 which is incorporated herein by reference. This method utilizes a packaging/transduction system with bacteriophage vectors.

The recombinant plasmids so produced can then be used to transform or "infect" cells in which the plasmid is compatible, resulting in introduction of the foreign gene into the cell. The recombinant plasmid must be capable of autonomous replication in the host cell and should have a marker function which allows the selection of host cells so transformed by the recombinant plasmid. If all of the proper replication, transcription and translation signals are correctly arranged on the plasmid, the foreign gene will be properly expressed in the transformed cells and their progeny.

2.2 Retroviruses

The Retroviridae family of RNA-containing tumor viruses is characterized by the presence of the enzyme, reverse transcriptase, in the virions. These viruses are able to infect and replicate only in their natural eucaryotic hosts. The genome of these viruses is composed of two single-stranded RNA molecules that replicate through a double-stranded DNA intermediate which is synthesized from the RNA molecules by the reverse transcriptase. Discovery of this enzyme was a decisive step in understanding the mechanism by which a virus with an RNA genome could replicate its genetic information in infected cells (Baltimore, 1970, Nature 226:1209; Temin and Mizutani, 1970, Nature 226:1211). Avian Sarcoma Virus (ASV), which is used in this invention as a source of the gene coding for the β-subunit of reverse transcriptase, is a member of the Retroviridae family.

Reverse transcriptase is an RNA-dependent DNA polymerase that elongates an oligonucleotide primer (such as a tRNA) paired to a template strand (either RNA or DNA) and thus synthesizes a DNA molecule that is complementary to the template strand (complementary DNA, cDNA). While ASV reverse transcriptase occurs in multiple molecular forms, the major molecular species is a heterodimer of two structually related polypeptide chains designated the α-subunit and the β-subunit (64,000 and 92,000 daltons, respectively). The heterodimer possesses multiple enzymatic activities including polymerizing activity, RNase activity (RNase H is an exonuclease that degrades the RNA of DNA-RNA hybrids) and DNA endonuclease activity. The polymerase activity and RNase H activity have been ascribed to the α-subunit and to other molecular forms, such as a dimer of the β-chain (Hizi, 1977, J. Biol Chem. 252:2281). Tryptic fingerprint analysis has demonstrated that the α-subunit may be derived proteolytically from the β-subunit (Verma, 1977, Biochim. Biophys. Acta 473:1). Another polypeptide possessing endonuclease activity, p32, has been shown to be structurally related to the β-subunit but not to the α-subunit.

Amino acid sequence analysis indicates that the β-chain consists of the α-subunit and p32 (Copeland et al., 1980, J. Virol. 36:115). Although each subunit has a polymerase activity, the α-subunit does not bind as well as the β-subunit (Gerard and Hrandgenett, *Molecular Biology of RNA Tumor Viruses*, Ed., J. R. Stephenson, Academic Press, New York, N.Y., 1980; Copeland et al., 1980, J. Virol. 36:115 Hizii, 1977 J. Biol. Chem. 252:2281).

Techniques currently used for producing reverse transcriptase involve isolating the enzyme from virus particles which contain about thirty reverse transcriptase molecules per virion (Kacian et al., 1971, Biochim. Biophys. Acta 246:365).

Although the entire nucleotide sequence of the ASV genome has been determined for Prague C ASV (Schwartz, 1981, Cold Spring Harbor RNA Tumor Virus Meeting, Cold Spring Harbor, N.Y.), molecular cloning of the reverse transcriptase gene alone has not heretofore been described. Comparison of the nucleotide sequence of the entire ASV genome to the DNA sequence predicted from the amino acid sequence analysis of reverse transcriptase (Gerard and Grandgenett, *Molecular Biology of RNA Tumor Viruses*, Ed., J. R. Stephenson, Academic Press, New York, N.Y., 1980; Copeland et al., 1980, J. Virol. 36:115) affords a means for identifying the location of the amino-terminal coding sequence of the reverse transcriptase gene within the ASV genome. Utilizing these methods it has become possible to isolate the gene coding for ASV reverse transcriptase.

2.3 Gene Expression

As is characteristic of all viruses which infect eucaryotic cells, ASV requires a eucaryotic host cell system in which to replicate its genome, express viral genes, and generate its progeny. The signals and control elements for replication, expression, and viral packaging in eucaryotes differ from those of procaryotes. This is of critical importance when attempts are made to express in procaryotic host cells a gene which is naturally expressed only in eucaryotic cells.

These different genetic signals and processing events control gene expression at two levels, DNA transcription and messenger RNA translation. Transcription of DNA is dependent upon the presence of a promoter which is a DNA sequence that directs the binding of RNA polymerase and thereby promotes transcription. The DNA sequences of eucaryotic promoters differ from those of procaryotic promoters. Furthermore, eucaryotic promoters and accompanying genetic signals may not be recognized or function in a procaryotic system.

Similarly, translation of messenger RNA (mRNA) in procaryotes depends upon the proper procaryotic signals which differ from those of eucaryotes. Efficient translation of mRNA in procaryotes requires a ribosome binding site called the Shine Dalgarno (SD) sequence on the mRNA. This SD sequence is a short nucleotide sequence of mRNA that is located before the start codon (AUG) which encodes the amino-terminal methionine of the protein. The SD sequences are complementary to the 3' end of the 16S rRNA (ribosomal RNA) and probably promote binding of mRNA to ribosomes by duplexing with the rRNA to allow correct positioning of the ribosome.

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in *E. coli* and other bacteria. This protein-degrading system appears to selectively destroy "abnormal" or foreign proteins, such as eucaryotic proteins. A tremendous utility, therefore, would be afforded by the development of a means to protect eucaryotic proteins expressed in bacteria from proteolytic degradation.

One strategy to promote the expression of eucaryotic genes in procaryotes is to construct hybrid genes in which the eucaryotic sequence is fused in phase (in the same reading frame) to a procaryotic gene resulting in a fusion protein product (a protein that is a hybrid of procaryotic and eucaryotic amino acid sequences). This approach has been used in the molecular cloning of a number of eucaryotic proteins, such as somatostatin (Itakura et al., 1977, Science 198:1056), rat proinsulin (Villa-Komaroff et al., 1978, Proc. Natl. Acad. Sci., U.S.A. 75:3727), growth hormone (Seeburg et al., 1978, Nature 276:795), and ovalbumin-like protein (Mercereau-Puijalon et al., 1978, Nature 275:505). Additionally, procaryotic promoters have been fused to such fusion genes in the case of ovalbumin (Fraser et al., 1978, Proc. Natl. Acad. Sci., U.S.A. 75:5936) and β-globin (Guarente et al., 1980, Cell 20:543). The Guarente et al. system involves inserting the lac promoter, including the SD sequence, at varying distances in front of the ATG start codon of the fusion gene. Although the molecular cloning and expression of several eucaryotic genes has been accomplished, this has not heretofore been done for the reverse transcriptase gene. Nor is the state of the art such that expression of foreign, eucaryotic genes in procaryotic host cells may be routinely performed.

ASV reverse transcriptase plays a central role in the recombinant DNA cloning process. Reverse transcriptase is useful for making cDNA from either single stranded RNA or DNA. This cDNA can be inserted into a vector as a potentially functional gene. The expression of eucaryotic genes in *E. coli* requires that the coding sequence of the gene of interest be available in a form uninterrupted by intervening sequences. During mRNA processing in eucaryotes, these introns are spliced out of the mRNA prior to translation. Reverse transcriptase is able, under proper conditions and in the presence of proper substrates, to transcribe the mRNA into a double-stranded DNA copy (cDNA), thus generating a gene free from intervening sequences which is capable of serving as a template for the production of a functional eucaryotic protein in a procaryotic (or eucaryotic) host cell. Isolation and/or synthesis of DNA free from intervening sequences is a requirement for eucaryotic gene expression of an active protein in procaryotic cells. The large quantities of pure and active reverse transcriptase generated in the system herein disclosed can fulfill the current need for this enzyme in the rapidly expanding field of recombinant DNA technology.

3. SUMMARY OF THE INVENTION

Methods and compositions are provided for the cloning and expression of the β-subunit of Avian Sarcoma Virus (ASV) reverse transcriptase gene in host microorganisms. Also described are methods for culturing these novel microorganisms to produce the β-subunit of reverse transcriptase. Additionally, the characterization and isolation of a metabolically stable and biologically active product of the cloned reverse transcriptase gene is described.

The ASV reverse transcriptase gene was identified in the ASV genome by nucleotide sequence predictions made from protein sequence analysis of the β-subunit of reverse transcriptase and by DNA-protein length comparisons. Utilizing these sequence and length determinations as guides, the reverse transcriptase gene, or a major portion thereof, may be selectively isolated from DNA carrying the entire ASV genome. Restriction endonuclease cleavage may be performed at specific sites within the ASV genome so as to isolate the desired fragment containing the reverse transcriptase gene.

The isolated reverse transcriptase gene or gene fragment was subsequently inserted into a plasmid vector which serves as a biologically functional replicon. This plasmid, containing the reverse transcriptase gene, was constructed so as to facilitate both the replication and expression of the reverse transcriptase gene upon transformation of compatible host cells. Additionally, the plasmid provided for a one-step identification of transformed microorganisms actively expressing the reverse transcriptase gene. In those instances where a portion of the complete gene is isolated and cloned, reconstruction of the complete reverse transcriptase gene is performed.

The present invention may be more fully understood by reference to the following detailed description of the invention, examples of specific embodiments of the invention and the appended figures (not drawn to scale) in which:

FIG. 3b is a graphic representation of the elution profile, plotted as $CPM \times 10^{-3}$ versus fraction number, from a phosphocellulose column of pooled fractions resulting from the chromatography depicted in FIG. 3a.

4. DESCRIPTION OF THE INVENTION

This invention relates to the production of reverse transcriptase using recombinant DNA techniques. Recombinant plasmids constructed as described herein provide a protein having reverse transcriptase activity which is stable and degradation-resistant; such plasmids enable the generation of large quantities of pure and active reverse transcriptase.

The process of this invention may be divided into the following stages for the purposes of description: (1) identification and isolation of the reverse transcriptase gene, (2) insertion of the reverse transcriptase gene into a cloning vector, (3) insertion of transcriptional and translational signals into the recombinant plasmid, (4) culturing the transformed microorganisms capable of expressing reverse transcriptase, (5) identification of the reverse transcriptase gene product and (6) isolation of pure reverse transcriptase.

4.1 Identification and Isolation of the Reverse Transcriptase Gene

The reverse transcriptase gene (or the genetic information contained therein) can be obtained from a number of different sources. For instance, the gene may be obtained from retrovirus, eucaryotic cells which are infected with retrovirus, or from a number of plasmids which contain either a portion of or the entire retrovirus genome.

Once the total DNA is isolated from any of these sources using standard isolation techniques, the DNA is cleaved into linear fragments, any one of which may contain the gene for reverse transcriptase. Such fragmentation may be achieved using enzymes which digest or cleave DNA, such as restriction enzymes which cleave DNA at specific base sequences, or by physically shearing the DNA. After the linear DNA fragments are generated, they are separated according to size by standard techniques including agarose and polyacrylamide gel electrophoresis and column chromatography.

Identification of the DNA fragment which contains the gene may be accomplished in a number of ways. For example, it is possible to sequence the DNA fragments (Maxam and Gilbert, 1980, *Methods in Enzymology* 65:499) to identify which fragment contains the reverse transcriptase gene. Alternatively, hybridization techniques (Southern, 1975, *J. Mol. Biol.* 98:503) using a labeled (e.g., radioactively labeled) DNA probe may be employed.

Once the DNA fragment containing the reverse transcriptase gene has been identified, a large quantity (nanogram amounts) of this fragment is isolated. This is accomplished by growing on a large scale the source of the reverse transcriptase gene, e.g., retrovirus, viral infected cells, or bacteria containing the viral genome in recombinant plasmids. The viral or plasmid DNA is isolated, fragmented, fractionated and sized on a preparative scale by the same methods previously used to locate the gene.

An alternative to isolating the reverse transcriptase gene from a retroviral genome is to make cDNA to the mRNA which codes for reverse transcriptase. To this end, mRNA coding for reverse transcriptase is isolated from viral infected cells. By standard techniques the isolated mRNA is then converted into cDNA using reverse transcriptase. The cDNA can then be inserted into a plasmid vector in a conventional manner.

In the embodiment of the examples, the reverse transcriptase gene was obtained from pRSV60 (Highfield et al., 1980, J. Virol. 36:271) which contains only part (3824 b.p.) of the complete ASV genome but all of the reverse transcriptase gene. The DNA fragments of pRSV60 were generated by restriction digests and fractionated by agarose gel electrophoresis (Johnson, 1977, Biochemistry 16:4217). Those DNA fragments believed to contain the reverse transcriptase gene or a portion thereof were isolated by electroelution and partially sequenced (Maxam and Gilbert, 1980, Methods In Enzymology 65:499). These sequences were compared to the predicted DNA sequence of reverse transcriptase which was derived from the partially known partial amino acid sequence of the enzyme as reported by Copeland et al. (1980, J. Virol. 36:115).

In the examples of the present application, the restriction enzymes used for fragmentation were Bgl II and Eco RI. The DNA fragment isolated contained two-thirds of the reverse transcriptase gene. The ends of this gene fragment were modified in order to tailor the gene fragment for insertion into a suitable vector.

Any restriction enzyme or combination of restriction enzymes may be used provided the enzyme does not destroy the reverse transcriptase gene. For example, one could employ Pst I or Eco RI alone or in combination with Xba I, Bam HI or Bgl II in order to isolate a suitable portion of the reverse transcriptase gene. If the complementary restriction sites are not present in the cloning vector, then the ends of the excised gene (or of the cleaved vector) must be modified. Such modifications include producing blunt ends (digesting back single strands of DNA or filling in with *E. coli* polymerase I or T4 DNA polymerase), and linker ligation (ligating poly dC/dG or poly dA/dT tails or specific restriction linkers onto DNA ends). Generally, the restriction enzymes used for gene isolation are selected with the gene location and cloning vector in mind.

4.2 Insertion of the Reverse Transcriptase Gene into a Cloning Vector

Once isolated, the reverse transcriptase gene or gene fragment is inserted into an appropriate cloning vector which will provide a means for replicating the gene. Any appropriate cloning vector containing a marker function may be used, for example, SV40 DNA, bacteriophage vectors such as lambda gt WES-lambda B, Charon 28, Charon 4A, lambda gt lambda BC, lambda gt1-lambda B, or M13mp7, or other plasmid DNA vectors, such as pBR322, pAC105, pVH51, PACY177, pKH47, pACYC184, pUB110, pMB9, pBR325, ColE1, pSC101, pBR313, pML21, RSF2124, pCR1, or RP4. If the cloning vector does not have restriction sites complementary to the ends of the reverse transcriptase gene fragment, then the ends of the gene fragment or the vector may be modified as previously described.

Insertion of the fragment into the vector is accomplished by cleaving the vector with restriction enzymes which yield cohesive ends that are complementary to those of the gene fragment (or modifying these ends so that they are complementary) and then ligating the two fragments. When the DNA gene fragment contains a blunt end, the gene may be ligated to a blunt-ended linearized vector.

In the example of the present invention pLG200, pLG300 and pLG400 (Guarente et al., 1980, Cell 20:543) were used as vectors. These three plasmids allow for fusion of the 3' terminus of the reverse transcriptase gene to the 5' terminus of the β-galactosidase hybrid gene in the pLG vectors. Thus, the order of the genes in the direction of translation is reverse transcriptase followed by β-galactosidase.

The three pLG plasmids contain a hybrid gene consisting of a fragment of the lacI gene fused to the lacZ gene which is missing the first twenty-three codons. The hybrid gene codes for a single protein containing amino acid sequences corresponding to both lac repressor (lacI) and β-galactosidase (lacZ) genes The promoter/operator region of DNA which is normally present between the lacI and lacZ genes has been deleted. Throughout the present application, the hybrid lacI-lacZ gene will be referred to as the lacZ or β-galactosidase gene.

The pLG plasmids allow for fusion of the reverse transcriptase gene into three possible reading frames, only one of which will allow translation of the reverse transcriptase gene in the same reading frame as the hybrid lacZ gene. As a result of this ligation in the example of the present invention, a region of the reverse transcriptase gene coding for the amino terminal portion of the protein (lacking the termination sequence) was fused to DNA coding for the enzymatically active carboxy terminal portion of the β-galactosidase gene located in the pLG plasmids. Although gene fusion technology is not a requirement for the practice of this invention, it is advantageous. In the present examples, gene fusion may add to the stability of the gene product in the transformed cell and cell extract, and provides a convenient, simple assay for expression of gene product.

Once ligated, the recombinant plasmid is used to transform the appropriate host cells. The host cell types used for transformation depend on the cloning vector, that is, the vector must be capable of replication in the host cell and must be otherwise compatible with the host cell. For the purposes of the examples contained herein, *E. coli* was chosen as the host. Transformants are selected based upon the expression of appropriate gene markers normally present in the vector, such as ampicillin resistance or tetracycline resistance in pBR322. Expression of such marker proteins indicates that the plasmid is intact and is replicating. In the present examples, these recombinant fusion plasmids contain the ampicillin resistance gene, so only clones that grow in the presence of ampicillin are selected.

4.3 Insertion of a Promoter into the Cloning Vector

In order to obtain efficient expression of the foreign gene, a promoter is inserted into the recombinant plasmid at a site before the 5' terminus of the reverse transcriptase gene sequence. RNA polymerase normally binds to the promoter and initiates transcription of a group of linked genes and regulatory elements, called an operon. Promoters vary in their "strength", i.e., their ability to promote transcription. For the purpose of molecular cloning it is desirable to insert strong promoters in order to obtain a high level of transcription and, hence, expression of the gene. In the present invention, the lac promoter was inserted. However, depending upon the host cell system utilized, any one of a number of other suitable promoters may be inserted. For instance, when cloning in an E. coli host cell system, any of the promoters isolated from E. coli, its bacteriophages or plasmids may be used. Additionally, E. coli promoters produced by recombinant DNA or other synthetic DNA techniques may be inserted to provide for transcription of the inserted gene. More specifically, the $P_R$ and $P_L$ promoters of coliphage lambda direct increasingly higher levels of transcription of adjacent DNA segments. In addition, the recA promoters from E. coli provide high levels of gene transcription of adjacent fragments.

According to the invention, a restriction site which is unique to the recombinant plasmid (i.e., a single such cleavage site exists in the plasmid) is created at a location before the 5' terminus of the inserted reverse transcriptase gene. The unique restriction site may have either cohesive ends (e.g., from the action of Eco RI, Bam HI, Sal I, etc.) or blunt ends (e.g., from the action of Hae III, Sma I, etc.). The unique restriction site is produced by opening the plasmid at an appropriate site, modifying the ends to accept synthetic DNA "linkers", and ligating the modified ends to form a plasmid containing the desired unique restriction site. If, however, the cloning vector already contains a unique restriction site in the correct position, this step can be eliminated.

Once a unique restriction site is present in front, i.e., before the 5' terminus, of the inserted reverse transcriptase gene segment, the recombinant DNA molecule is cleaved at this site, and progressively digested. Subsequently, a fragment of another DNA sequence containing a promoter and other genetic signals with appropriate termini is inserted.

Any method used to insert any DNA fragment or gene into a vector may be used for inserting the promoter into the unique site of the recombinant plasmid (e.g., the use of restriction enzymes to create compatible cohesive ends on the fragment and on the vector which are then combined in the ligation mix; or the use of restriction enzymes to create blunt ends on the fragment and vector which can then be blunt end ligated; or modification of the existing ends on the DNA fragment or plasmid by linker ligation).

Specific initiation signals are required for efficient gene transcription and translation in procaryotic and eucaryotic cells. These transcription and translation initiation signals may vary in "strength" as measured by the quantity of gene-specific message and protein synthesized, respectively. The promoter-bearing DNA fragment inserted at the unique site may contain any combination of variously "strong" transcription and/or translation initiation signals. In the specific examples of the invention, the translation initiation signal, specifically the SD-ATG combination, is derived from the E. coli lac operon. Other suitable SD-ATG combinations that can be utilized by E. coli ribosomes may be employed, such as the SD-ATG combinations associated with the cro or N genes of coliphage lambda, or from the E. coli tryptophan E, D, C, B or A genes. Additionally, any SD-ATG combination produced by recombinant DNA or other synthetic technique may be used.

In the example of the present invention the lac promoter fragment from a UV5 mutant was inserted. This fragment consists of a mutant CAP binding site, the RNA polymerase binding site, the ribosome binding site (Shine Dalgarno sequence) and the initiating ATG sequence. This lac promoter fragment was obtained from the pMGI101 plasmid (approximately 10,000 base pairs), which is a pBR322 derivative containing a modified lac operon. In practice, a functional lac promoter may be obtained from any appropriate source (e.g., bacterial chromosome or a recombinant plasmid) which contains the lac operon.

The promoter fragment is inserted into the recombinant plasmid at varying positions with respect to the beginning of the reverse transcriptase gene in order to obtain one product plasmid in which translation of the reverse transcriptase gene occurs in phase with respect to the start codon of the inserted fragment (i.e., in the proper reading frame). To accomplish this, after cleaving the plasmid at its unique restriction site, the linear DNA is progressively digested from the ends to produce a population of linear plasmid DNA molecules of varying lengths. The lac promoter-bearing DNA fragment is ligated into the plasmid and the resultant ligation mix is used to transform bacteria. This results in positioning the lac promoter fragment at varying distances from the 5' terminus of the reverse transcriptase/β-galactosidase fusion gene.

Transformants are screened for fusion protein activity as an indication that the start codon of the promoter fragment was positioned in an appropriate reading frame with the fusion gene. In the example contained herein, bacterial clones are screened for β-galactosidase activity by the method of Miller (*Experiments in Molecular Genetics*, Cold Spring Harbor Press, New York, N.Y., 1972). The intensity of the resultant color in this assay is an approximation of the relative efficiency of expression of the fusion protein. Positive clones (those demonstrating β-galactosidase activity) can then be further assayed for fusion protein production by immunoassay and by polypeptide analysis. In the preferred embodiment a polypeptide of the expected molecular weight of the fusion protein is identified (e.g., by gel electrophoresis) that cross reacts with antibody directed against reverse transcriptase and with antibody directed against β-galactosidase.

4.4 Reconstruction of the Reverse Transcriptase Gene

In those instances where only a portion of the reverse transcriptase gene was ligated into the cloning vector, the missing portion of the gene must be inserted into the proper site in order to reconstruct the entire reverse transcriptase gene. In the specific example of the present invention, the region of the reverse transcriptase gene which codes for the carboxy terminal fragment of the protein and contains the proper termination codon is inserted. Obviously, this step is not required if the entire reverse transcriptase gene was originally inserted into the cloning vector.

According to the specific example of the present invention, the terminal portion of the reverse transcriptase gene was obtained by digesting pRSV60 with restriction endonucleases that excise the carboxy terminal half of the gene. This portion of the reverse transcriptase gene may be obtained from any of the sources previously mentioned. Any of a number of appropriate restriction enzymes may be used for this purpose. However, the restriction enzymes selected for use should create termini that are compatible with those of the cloning vector to allow insertion of this gene portion into the site in the reverse transcriptase gene fragment on the plasmid; otherwise the ends of the DNA fragment or plasmid should be modified for insertion. In the specific example of the present invention the restriction enzymes used on both the reverse transcriptase gene and cloning vector are Eco RI and Bam HI.

Reconstruction of the reverse transcriptase gene results in removal of the β-lactosidase gene, which was fused to the reverse transcriptase gene, and thus results in loss of fusion protein production. The resultant plasmid which now contains a promoter, the proper sequences for initiation and transcription and translation in procaryotes, and the complete reverse transcriptase gene sequence with its proper termination signals, is used to transform the appropriate host cells. After transformation, clones which are positive for the correct insertion may be identified by restriction enzyme analysis.

The protein product of the gene may be identified by analyzing crude or purified lysates of cells grown from transformed cells which, as demonstrated by restriction analysis, contain the correct insertion. However, if the microorganisms secrete the protein, reverse transcriptase may be identified in the medium. In the specific examples of the present invention identification of the reverse transcriptase protein (gene product) in cell lysates was accomplished by polypeptide analysis and immunoassay using monoclonal antibodies directed against Avian Myeloblastosis Virus (AMV) reverse transcriptase. However, other methods may be used, such as assay of reverse transcriptase activity.

4.5 Purification of Reverse Transcriptase

Transformed cells containing the plasmid having the reverse transcriptase gene are grown up in a large volume and the reverse transcriptase protein is isolated from such cells or from the medium if the protein is excreted. The protein isolated in the specific example of the present invention was the fully active, metabolically stable β-subunit of ASV reverse transcriptase; however, the techniques described in the present invention may be applied to any type of reverse transcriptase, such as the reverse transcriptase found in Cisternavirus A, Oncovirus B, Oncovirus C (such as mammalian or reptilian oncoviruses), Oncovirus D, Centivirus E or Spunavirus F.

5. EXAMPLES

5.1 Identification of the Reverse Transcriptase Gene

The DNA sequence (gene) coding for the ASV β-subunit of reverse transcriptase was isolated from the pRSV60 plasmid (approximately 8186 base pairs), a derivative of the parent clone lambda RPA101 (Highfield et al., 1980, J. Virol. 36:271). Lambda RPA101 contains the complete Prague A Avian Sarcoma Virus genome. The plasmid pRSV60 was constructed by inserting a 3824 base pair portion of the ASV genome (obtained from an Eco RI digest of lambda RPA101) into the Eco RI site of pBR322 (FIG. 2a).

The location of the 5' terminus of the reverse transcriptase gene (coding for the β-subunit) in pRSV60 was identified by restriction enzyme analysis and DNA sequencing. Plasmid DNA (pRSV60) was isolated using a method adapted from Guerry et al. (1973, J. Bacteriol. 116:1064). Accordingly, the isolated DNA was digested with the appropriate restriction endonucleases. The resulting restriction fragments were resolved by agarose gel electrophoresis (Johnson, 1977, Biochemistry 16:4217) and the DNA was isolated from selected bands. To achieve this, desired bands were cut out of the agarose gel, placed into dialysis tubing in electrophoresis buffer, and subjected to an electric field of 150 volts for 2 hours. The solution containing the DNA was removed from the dialysis bag and the DNA was isolated on DEAE-S2 resin (Maxam and Gilbert, 1980, Methods in Enzymology 65:499).

Figure 1:
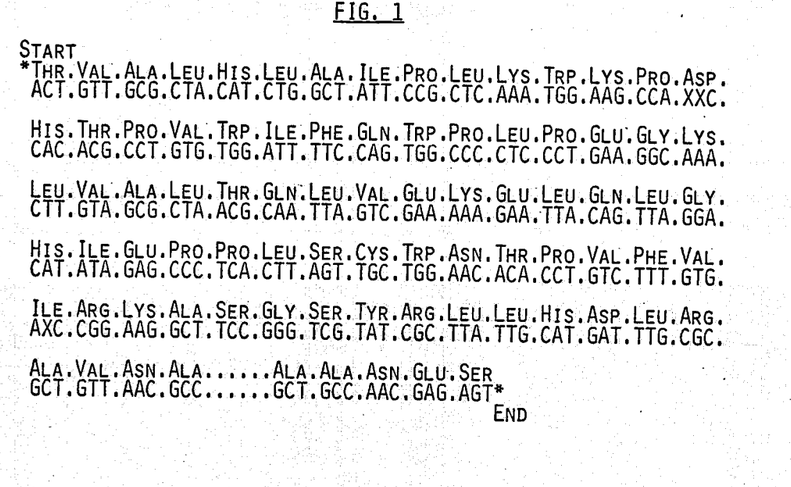
FIG. 1 represents the DNA sequence of the beginning and end of the reverse transciptase gene cloned in the present invention.

The isolated selected DNA fragments were sequenced according to the method of Maxam and Gilbert. The sequences obtained were compared to DNA sequences predicted from the known amino terminal of the amino acid sequences of reverse transcriptase (Copeland et al., 1980, J. Virol. 36:115) and carboxy terminal amino acid sequences of the gag protein (another ASV protein), as reported by Gerard and Grandgenet (Molecular Biology of RNA Tumor Viruses, Ed., J. R. Stephenson, Academic Press, New York, N.Y., 1980). The termination site of the reverse transcriptase gene fragment was approximated by DNA/protein length comparisons. FIG. 1 presents the DNA sequence of the beginning and end of the reverse transcriptase gene cloned in the present invention.

Figures 2A, 2B, 2C:
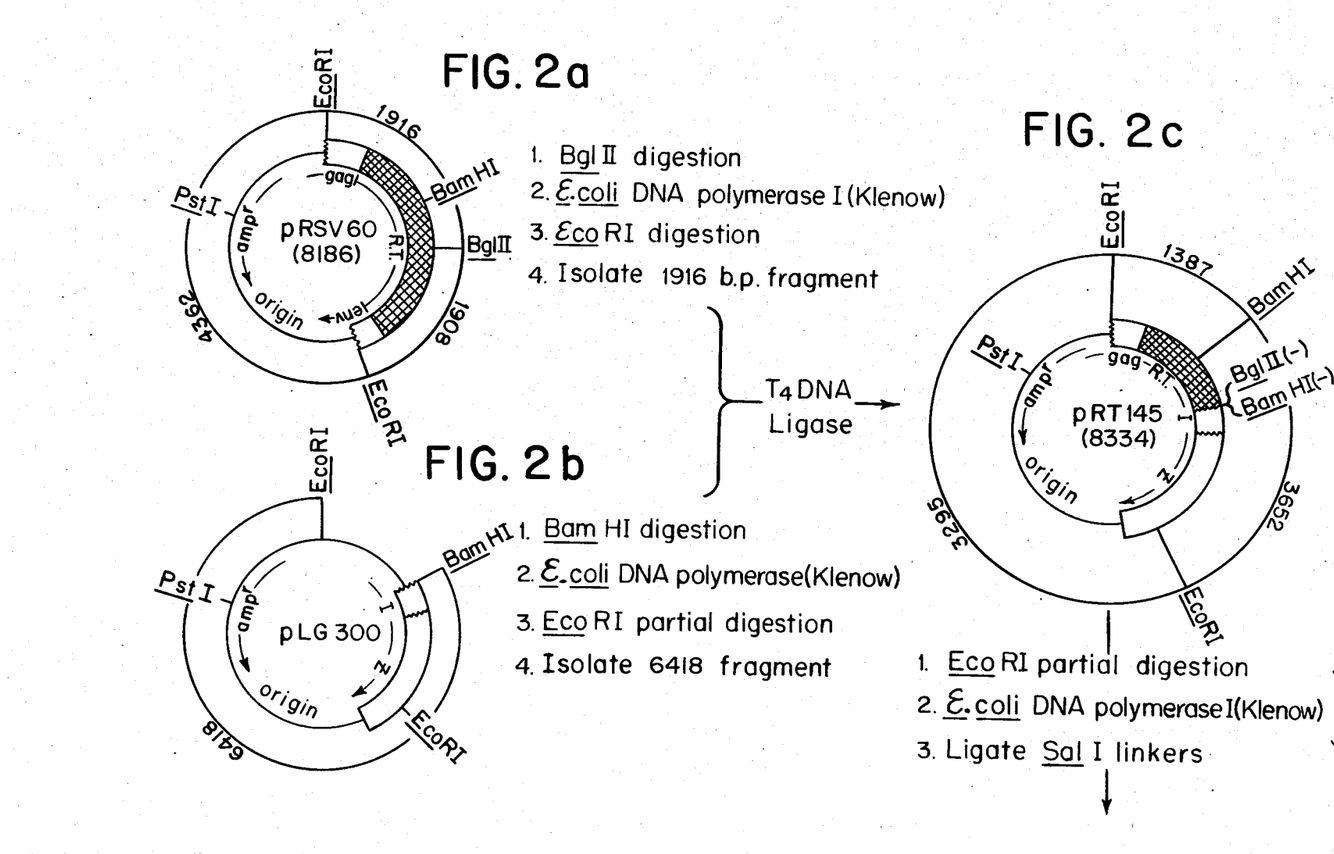
FIG. 2a represents a schematic map of the pRSV60 plasmid showing the portion of the ASV genome that was inserted into the Eco RI site of pBR322.
FIG. 2b represents a schematic map of pLG300.
FIG. 2c represents a schematic map of pRT145, a plasmid consisting of a portion of pLc300 and pRSV60.

Results of such analysis demonstrated that the ASV fragment (3824 base pairs) contained in pRSV60 is composed of the reverse transcriptase gene flanked by two other partial gene sequences, env and gag (FIG. 2a). The terminal portion of the gag gene flanks the 5' terminus of the reverse transcriptase gene, while a chain initiator sequence (ATG) followed by a partial envelope gene (env) flanks the 3' terminus of the reverse transcriptase gene fragment.

5.2 Isolation of the Reverse Transcriptase Gene

Once identified, the DNA fragment containing 5' terminus and first two-thirds of the reverse transcriptase gene was selectively isolated from cloned pRSV60 DNA by restriction enzyme digestion and preparative scale purification. This portion of the reverse transcriptase gene was later fused to the beginning of the β-galactosidase gene as described in Section 5.3.

5.2.1 Plasmid Isolation

Large quantities of the recombinant DNA plasmid, pRSV60, were isolated from cultures derived from E. coli cells that were transformed with pRSV60. E. coli was grown in M-9 broth (Miller, Experiments in Molecular Genetics, Cold Spring Harbor Press, New York, N.Y., 1972). Plasmids were isolated using a modification of the method of Guerry et al. (1973, J. Bacteriol. 116:1063). The Guerry et al. method was altered by the use of propidium iodide in the cesium chloride gradients (Guntaka et al., 1976, J. Mol. Biol. 106:337). Plasmid DNA recovered from the gradient was extracted with NaCl-H$_2$O saturated isopropanol to remove dye, ethanol precipitated, dissolved in 0.4 ml H$_2$O and reprecipitated in ethanol.

5.2.2 Isolation of the Reverse Transcriptase Gene from pRSV60

The isolated plasmid, pRSV60, was completely digested with the restriction endonuclease, Bgl II (New England Biolabs Inc., Beverly, Mass.), using the following reaction conditions: incubate 1 ug DNA with 0.5 units enzyme at 37° C. for 60 minutes in 20 ul buffer consisting of 60 mM NaCl, 10 mM Tris-HCl (pH 7.4), 10 mM MgCl$_2$ and 1 mM β-mercaptoethanol. Digestion was monitored to completion via agarose gel electrophoresis, and resulted in a single linear DNA fragment with Bgl II cohesive termini.

The Bgl II cohesive termini were rendered blunt-ended by filling in with the Klenow fragment of *E. coli* DNA polymerase I (New England Biolabs Inc., Beverly, Mass.) in a reaction buffer consisting of 5 mM MgCl$_2$, 10 mM β-mercaptoethanol, 50 mM Tris-HCl (pH 8.1), 2 mM dNTP and an enzyme concentration of 3 units/0.05 ml. This resulted in elimination of the Bgl II cohesive termini and the creation of blunt ends on the DNA fragment. These blunt ends are labeled Bgl II(−) herein.

Finally, the linearized, blunt-ended pRSV60 DNA was totally digested with the restriction endonuclease, Eco RI (New England Biolabs, Inc., Beverly, Mass.), using the following reaction conditions: incubate 1 ug DNA with 0.5 units enzyme at 37° C. for 60 minutes in 20 ul buffer consisting of 10 mM Tris-HCl (pH 7.5), 50 mM NaCl and 5 mM MgCl$_2$. When analyzed by agarose gel electrophoresis, three DNA bands were visualized. The DNA band corresponding to the reverse transcriptase gene fragment (1916 base pairs) was isolated from the gel. This DNA fragment, containing the first two-thirds of the reverse transcriptase gene, has an Eco RI cohesive terminus at the 5' end and is blunt-ended [Bgl II(−)] at the 3' terminus. The region coding for the carboxy terminus of reverse transcriptase, the termination codon and the partial envelope gene originally present in pRSV60 are not contained in this isolated DNA fragment (FIG. 2a).

5.3 Production of Fusion Gene

The 3' terminus of the reverse transriptase gene fragment isolated in Section 5.2.2 was fused to the 5' terminus of the *E. coli* β-galactosidase gene (lacZ gene) in three lacZ fusion plasmids, pLG200, pLG300 and pLG400 (Guarente et al., 1980, Cell 20:543). These three plasmids allow for three possible fusion positions of a given fragment with respect to the correct reading of the β-galactosidase gene. Only one of these will allow full in phase translation of the fused reverse transcriptase/β-galactosidase gene. Once expression is achieved, the fusion gene may provide stability to the reverse transcriptase gene product, and allow a simple means of measuring the relative level of gene expression. However, at this stage the fused gene is, in general, neither transcribed into mRNA nor translated into protein.

5.3.1 Preparation of the pLG Plasmids

Two of the plasmids, pLG200 and pLG400, were totally digested with the restriction endonuclease, Hind III, while pLG300 was totally digested with Bam HI (New England Biolabs, Inc., Beverly, Mass.). Such treatment results in cleavage of each of the three plasmids at the lacI gene. The following reaction conditions were used: incubate 1 ug DNA with 0.5 units enzyme at 37° C. for 60 minutes in 20 ul buffer. The Bam HI buffer consisted of 150 mM NaCl, 6 mM Tris-HCl (pH 7.5) and 6 mM MgCl$_2$; the Hind III buffer consisted of 60 mM NaCl, 7 mM MgCl$_2$ and 7 mM Tris-HCl (pH 7.5). The cohesive termini of the restriction sites were filled in using the Klenow fragment of *E. coli* DNA polymerase I (as previously described in Section 5.2.2) and are labeled Bam HI(−). FIG. 2b depicts pLG300.

Each of the linear pLG DNA molecules was then partially digested with Eco RI. Partial digestions were accomplished by modifying the conditions used for total digestion as follows: 0.5 unit of enzyme was incubated with 1 ug of DNA at 37° C. and aliquots (1/10 volume) were removed at 5 minutes intervals, at which time 0.1% sodium dodecyl sulfate (SDS) was added to the aliquot in order to stop the reaction. Thus, the reaction conditions were adjusted to obtain an average of one cleavage per DNA molecule. The DNA fragments of the appropriate size were isolated from preparative agarose gels by electroelution and purified as previously described. More specifically, the DNA fragment isolated was approximately 6418 base pairs (b.p.) and contained both the lacZ and ampicillin resistance (amp$^r$) genes (FIG. 2b). The 5' terminus of the lacZ gene was blunt-ended while the opposite end of the linearized plasmids contained an Eco RI cohesive end (FIG. 2b).

5.3.2 Ligation of the Reverse Transcriptase Gene Fragment into pLG200, pLG300 and pLG400

The pRSV60 DNA fragment isolated in Section 5.2.2 (containing two-thirds of the reverse transcriptase gene as measured from the 5' terminus) and the prepared pLG200, pLG300 and pLG400 fragments were ligated in a 10:1 molar ratio using T4 DNA ligase New England Biolabs Inc., Beverly, Mass.). DNA ligation was carried out in 10–15 ml ligase buffer consisting of 50 mM Tris-HCl (pH 7.5), 10 mM MgCl$_2$, 20 mM dithiothreitol, 1 mM ATP and a DNA concentration ranging from 15–20 ug/ml. Ligation reactions were incubated overnight at room temperature using $3 \times 10^2$ units of T4 DNA ligase per 10 ul reaction volume.

The plasmids resulting from ligation were used to transform MC1000 (*E. coli* K12 strain) by the procedure of Bolivar and Backman (1979, *Methods in Enzymology* 68:245) and clones were screened for ampicillin resistance.

Ampicillin resistant colonies were analyzed for the presence of RSV60 DNA by the hybridization method of Chang et al. (1978, Nature 275:617) using nick translated RSV60 DNA as the labeled probe (Kelly et al., 1970, J. Biol. Chem. 245:39; Maniatas et al., 1975, Proc. Natl. Acad. Sci., U.S.A. 72:1184). Nick translation is the method of choice for in vitro labeling of duplex DNA to high radiospecific activity. This method takes advantage of two of the several activities of *E. coli* DNA polymerase I: the 5' to 3' exonuclease activity and the 5' to 3' polymerase activity. In nick translation, the enzyme binds at a nick in one strand of duplex DNA. The 5' to 3' exonuclease activity then hydrolyzes nucleotides in the nicked strand, ahead of the advancing polymerase. The nick is thus moved (translated) along the strand. Since the rate of hydrolysis is equal to the rate of polymerization, there is no net synthesis. However, in the course of this exchange reaction, radioactive deoxynucleoside triphosphates present in the reaction mixture are incorporated into the DNA (Southern, 1975, J. Mol. Biol. 98:503).

Plasmid DNA isolated from mini-lysates of *E. coli* clones that were positive for RSV60 DNA in the hybridization assay were analyzed by restriction digests using Eco RI and Bam HI to determine the correct fusion clones. Complete digests, using Eco RI/Bam HI, of correctly fused plasmids resulted in the generation of three DNA fragments: 1387 b.p., 3295 b.p. and 3652 b.p. The correct fusion plasmids were labeled pRT143, pRT145 and pRT147, corresponding to pLG200, pLG300 and pLG400, respectively (FIG. 2c depicts pRT145), and are about 8334 base pairs in length.

5.4 Construction of a Unique Restriction Site in the Cloning Vector

A unique restriction site was inserted before the 5' terminus of the reverse transcriptase gene in fusion plasmids, pRT143, pRT145 and pRT147. The pRT plasmids were opened at the Eco RI restriction site prior to the 5' terminus of the reverse transcriptase gene fragment sequence and this site was converted to the unique restriction site, Sal I, by linker ligation as follows.

A partial Eco RI digest of pRT143, pRT145 and pRT147 resulted in a majority of plasmids that were cleaved at only one of the two Eco RI sites. The DNA molecules were separated by agarose gel electrophoresis and the single cleavage linear plasmids (8334 base pairs) were isolated by electroelution. The Eco RI cohesive termini were filled in by E. coli DNA Polymerase I (Klenow fragment), as previously described, thereby producing blunt ends. The blunt-ended linear DNA molecules were then ligated in the presence of a 100:1 molar excess of Sal I linkers (octomers) (Collaborative Research, Inc., Waltham, Mass.) using the standard ligation methods previously described.

The ligated DNA was used to transform E. coli. Total plasmid DNA was isolated from the population of transformed (i.e., ampicillin resistant) bacteria. The isolated plasmids were cleaved with the restriction enzyme, Sal I, and analyzed by preparative agarose gel electrophoresis to ensure that the Sal I site was inserted in a single location. Sal I sensitive plasmid DNA was isolated by electroelution, religated and used to transform E. coli.

Figure 2D:
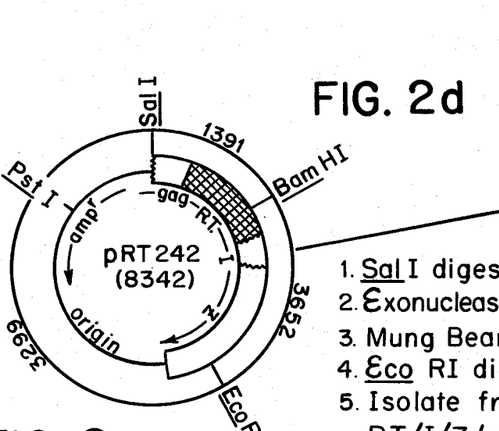
FIG. 2d represents a schematic map of pRT242, a plasmid derived from pR145, which differs by the creation of a unique (Sal I) restriction site.

Plasmids isolated from transformed E. coli (ampicillin resistant bacteria) were analyzed by restriction digests to ensure that the Sal I site was correctly positioned prior to (before) the start of the fusion gene. To achieve this, Bam HI/Sal I and Bam HI/Eco RI double digests were employed using reaction conditions previously described. The Sal I buffer consisted of 150 mM NaCl, 6 mM Tris-HCl (pH 7.5), 6 mM MgCl$_2$ and 0.6 mM β-mercaptoethanol. If the Sal I site is correctly positioned, then the Bam HI/Eco RI digest generates a 3652 b.p. and a 4690 b.p. DNA fragment, while the Bam HI/Sal I digest generates a 1391 b.p. and a 6951 b.p. DNA fragment. Those plasmids positive for the correct positioning of the Sal I site were identified as pRT241, pRT242 and pRT243 corresponding to pRT143, pRT145 and pRT147, respectively. FIG. 2d-depicts pRT242.

5.5 Insertion of the Lac Promoter into the Cloning Vector

The plasmids obtained in Section 5.4 were cleaved at the unique Sal I site, thus linearizing the pRT DNA. A limited terminal digestion of the linearized pRT DNA was performed using Exonuclease III followed by Mung Bean nuclease. Exonuclease III (Exo III) has a 3' phosphatase and double strand specific 3' exonuclease activity. Mung Bean nuclease digests single stranded DNA. Therefore, a digestion of the linearized pRT DNA with Exo III for a variable time followed by digestion with Mung Bean nuclease, resulted in a population of blunt-ended DNA molecules of varying lengths. This allowed insertion of the lac promoter fragment in varying positions on the plasmid with respect to the 5' terminus of the reverse transcriptase/β-galactosidase fusion gene as follows.

5.5.1 Progressive Digestion of pRT Linear DNA

The three plasmids, pRT241, pRT242 and pRT243, were cleaved at their unique restriction site by incubation with Sal I (New England Biolabs, Inc., Beverly, Mass.) using conditions recommended by the manufacturer.

The resulting linearized DNA molecules were then digested with Exonuclease III as follows: incubate 25 ug DNA at 25° C. in 100 ul of 66 mM Tris-HCl (pH 8.0), 0.66 mM MgCl$_2$ and 1.0 mM β-mercaptoethanol for 1, 2, 3, 5 and 10 minutes. These digestions were stopped by adding the DNA to buffer containing twice the recommended concentration of Mung Bean nuclease buffer (0.06M NaAcetate (pH 4.6), 0.10M NaCl, 2 mM ZnCl$_2$ and 10% glycerol). Then 300 units of Mung Bean nuclease (P. L. Biochemicals, Inc., Milwaukee, Wis.) per 200 ul of reaction volume was added to completely digest the single-stranded DNA, thus producing blunt-ended linear plasmid DNA of varying lengths. The reaction was stopped by phenol extraction using 100% phenol.

Figure 2E:
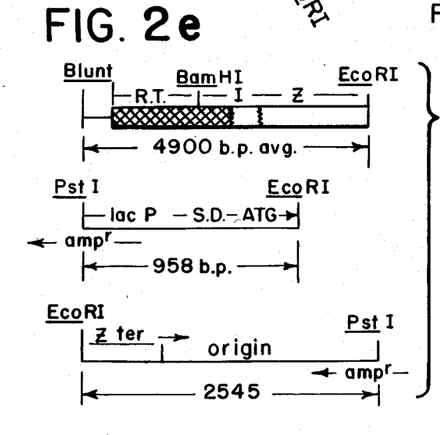
FIG. 2e represents a schematic map of three DNA fragments: the fusion gene, the lac promoter and the partial ampicillin resistance gene.

After ethanol precipitation the linear DNA was incubated with Eco RI (New England Biolabs, Inc., Beverly, Mass.) and the resulting DNA fragments were resolved by agarose gel electrophoresis. The DNA fragments of the appropriate sizes (average size of 4900 base pairs) that contained the reverse transcriptase fusion gene were isolated from the gel and purified as previously described. These purified DNA fragments containing the fused gene possess a blunt-end at the 5' terminus (i.e., the reverse transcriptase portion) and possess an Eco RI cohesive terminus at the 3' terminus (i.e., the β-galactosidase portion) (FIG. 2e).

5.5.2 Lac Promoter Insertion

The lac promoter DNA fragment was isolated by the simultaneous digestion of pMGI101 with Sma I and Pst I (New England Biolabs, Inc., Beverly, Mass.). pMGI101 is a plasmid which was constructed from pBR322 and the E. coli lac operon. After digestion of pMGI101, a 958 base pair DNA fragment containing the 5' portion of the ampicillin resistance (amp$^r$) gene, the lac promoter, Shine Dalgarno (SD) sequence and the initiation codon (ATG) was isolated by agarose gel electrophoresis. This fragment has a Pst I cohesive end located within the amp$^r$ gene before the promoter and a blunt end (Sma I site) located after the initiation codon (FIG. 2e).

In addition to the DNA fragments containing the fused reverse transcriptase gene (isolated in Section 5.5.1) and the DNA fragment containing the lac promoter (isolated from pMGI101), a third DNA fragment containing the 3' portion of the ampicillin resistance (amp$^r$) gene and the 3' terminus of the β-galactosidase gene was isolated as follows: DNA fragments derived by digesting whole plasmid pRT241 (or pLG200, pLG300 or pLG400) with Pst I and Eco RI were resolved on an agarose gel. The buffer for Pst I digestion consisted of 50 mM NaCl, 7 mM MgCl$_2$, 7 mM Tris-HCl (pH 7.5) and 6 mM β-mercaptoethanol. The appropriately sized fragments (2545 base pairs) which contain the partial amp$^r$ gene, the origin and the 3' terminal portion of the β-galactosidase gene were isolated from the gel. In these fragments the Pst I cohesive end is located at the partial amp$^r$ end, while the Eco RI cohesive terminus is located at the β-galactosidase end (FIG. 2e).

All three DNA fragments isolated in the present section were ligated in a 1:1:1 molar ratio. (The relative concentrations of each may be varied up to about one order of magnitude.) This was accomplished by incubating the lac promoter DNA fragment, the reverse transcriptase fusion gene DNA fragment and the ampicillin resistance gene DNA fragment with T4 DNA ligase as previously described. After ligation, the resulting plasmids were used to transform lac-negative E. coli.

Figure 2F:
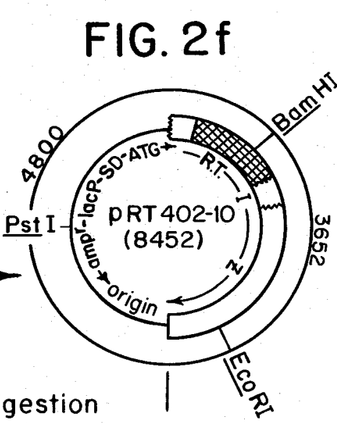
FIG. 2f represents a schematic map of the fusion gene plasmid, pRT402-10, which is the result of ligating the three DNA fragments of FIG. 2e.

Colonies of transformed E. coli (i.e., lac-positive bacteria) were screened using the β-galactosidase assay derived from Miller (*Experiments in Molecular Genetics*, Cold Spring Harbor Press, New York, N.Y., 1972). To this end E. coli were grown on β-galactosidase assay agar plates containing the dye x-gal (5-bromo-4-chloro-3-indolyl-β-D-galactoside). The colonies (clones) displaying a high level of β-galactosidase activity were isolated and catalogued. The lac promoter/reverse transcriptase/β-galactosidase recombinant plasmids derived from these clones were analyzed by restriction digests and designated pRT401, pRT402 and pRT403, corresponding to the original fusion protein plasmids from which they were derived (pRT241, pRT242 and pRT243, respectively). FIG. 2f depicts one such plasmid, pRT402.

5.6. Fusion Protein Assays

The E. coli transformants obtained in Section 5.5 were screened for reverse transcriptase/β-galactosidase fusion protein production by polypeptide analysis and by immunoassay, as follows:

5.6.1 Polypeptide Analysis

The estimated molecular weight of the fusion protein (178,653 daltons) was derived by adding the molecular weights of β-galactosidase (115,000 daltons) and two-thirds of the β-subunit of the reverse transcriptase protein (63,653 daltons).

Total cell lysates were prepared according to standard procedures from fifty different clones derived from each of the three fusion protein E. coli transformants produced in Section 5.5 (i.e., E. coli transformed with pRT401, pRT402 and pRT403). The protein isolated from these cell lysates was analyzed by SDS-polyacrylamide gel electrophoresis according to standard methods (Laemmli, 1970, Nature 227:680). Of the 150 different cell lysates screened, only those derived from the pRT402 transformants contained the predicted 178,653 dalton fusion protein.

5.6.2 Immunoassay

The clones producing the fusion protein were also screened for expression of the antigenically active peptide of the β-subunit of reverse transcriptase by immunoprecipitation techniques using both monoclonal antibody directed against AMV reverse transcriptase and whole antisera directed against β-galactosidase. Cell lysates of E. coli transformed with pRT402 reacted immunologically with both antibody preparations. Cell lysates of control E. coli (i.e., not transformed with pRT402) were negative for both. Thus, immunoprecipitation data confirmed the presence of a unique protein containing both reverse transcriptase and β-galactosidase antigenic determinants.

5.7 Reconstruction of the Reverse Transcriptase Gene

In order to obtain expression of a complete and active reverse transcriptase protein, it was necessary to reconstruct the entire reverse transcriptase gene by inserting its carboxy terminal portion in the correct position, as follows:

Plasmid DNA was isolated from the E. coli clone analyzed in Section 5.6 that was the strongest fusion protein producer (E. coli/PRT402-10). The isolated pRT402-10 DNA (8452 b.p.) was completely digested with Bam HI (New England Biolabs, Inc., Beverly, Mass.). The linearized DNA was then partially digested with Eco RI using conditions that allow each DNA molecule to be cleaved at one Eco RI site (as described previously). The resulting DNA fragments were analyzed by agarose gel electrophoresis and the appropriate DNA fragment (4800 b.p.) was isolated by methods previously described. This 4800 base pair fragment contains the ampicillin resistance gene, the lac promoter and approximately one-half of the 5' portion of the reverse transcriptase gene. A Bam HI cohesive end is located at the terminus in the reverse transcriptase gene while an Eco RI cohesive terminus is located at the opposite end of the fragment which is located within the β-galactosidase gene (see FIG. 2g).

Figure 2G:
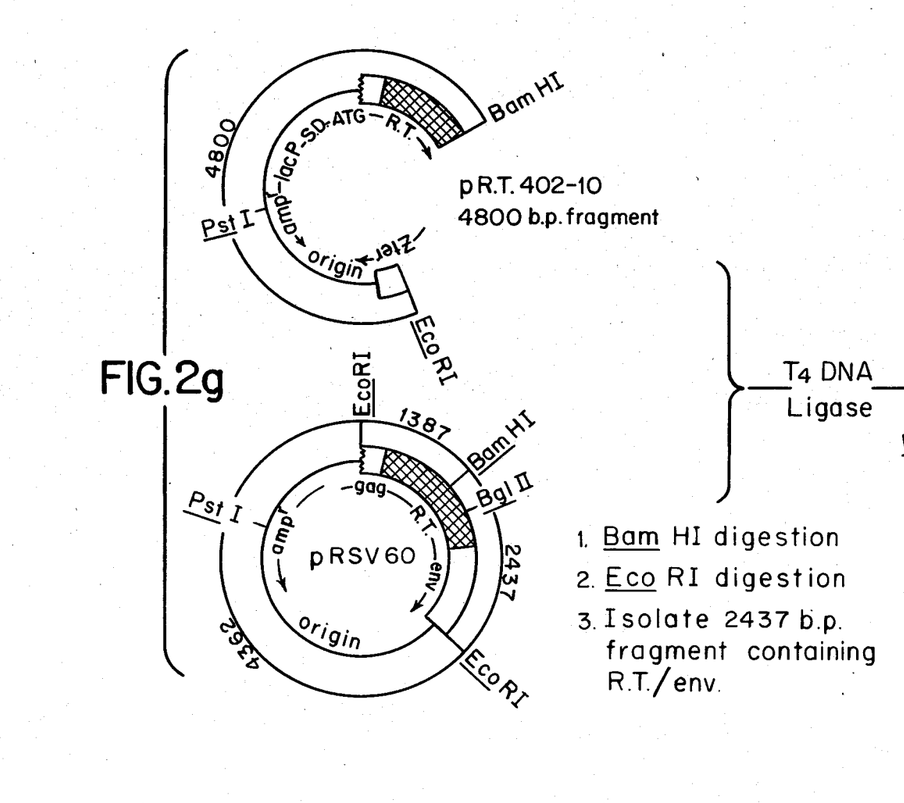
FIG. 2g represents a schematic map of pRSV60 showing the portion of the ASV genome which was used to reconstruct the reverse transcriptase gene.

Plasmid pRSV60 was digested to completion with Bam HI and Eco RI and the product fragments analyzed by agarose gel electrophoresis. A 2437 b.p. DNA fragment that encodes the carboxy terminal half of reverse transcriptase and a portion of the env gene was isolated from the gel by procedures previously described. The fragment is characterized by a Bam HI cohesive end at its amino coding terminus and an Eco RI cohesive end at its other terminus (FIG. 2g).

Figure 2H:
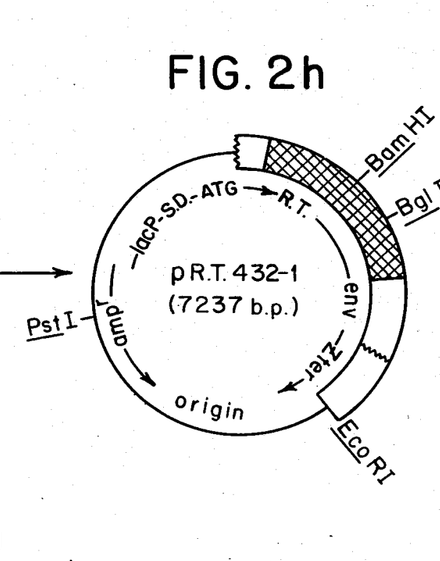
FIG. 2h represents the schematic map of pRT432-1 which contains the complete sequence coding for the β-subunit of the reverse transcriptase gene under the control of the lac promoter.

The two DNA fragments isolated in the present section contain both halves of the reverse transcriptase gene with complementary Bam HI ends. These fragments were ligated at a 1:1 ratio using DNA ligase under conditions previously described. After ligation (FIG. 2h) the plasmid, now called pRT432-1 corresponding to pRT402-10 from which it was derived, was used to transform E. coli K12 strain. The transformed organism has been deposited with the American Type Culture Collection, Rockville, Md. and has been assigned accession No. 31990.

Clones of E. coli transformants which were positive for the correct insertion of the ligated DNA plasmid were identified by restriction digest analysis of isolated plasmid. The completed plasmid has approximately 7237 base pairs.

5.8 Identification of the Reverse Transcriptase Gene Product

Immunoprecipitation analysis using monoclonal antibody against AMV reverse transcriptase was used with $^{35}$S-labeled extract of both the host E. coli (non-transformants) and transformed E. coli (i.e., E. coli carrying the pRT432-1 plasmid of Section 5.7).

5.8.1 Preparing the Cell Lysate

The noted E. coli were cultured overnight at 30° C. in M-9 broth to a cell density of about $5 \times 10^8$ cells/ml. A 1 ml aliquot was removed from each culture and centrifuged at $4000 \times g$ for 5 minutes at 4° C. The resultant pellet of cells was resuspended in 2 ml M-9 broth, methionine-free media. After incubation at 30° C. for 60 minutes $^{35}$S-methionine was added to the suspension at 100 uCi/ml. The cell suspension was then incubated at 30° C. for 30 minutes and centrifuged at 4000×g for 5 minutes at 4° C. The resultant pellet was resuspended in 1 ml of 10 mM Tris-HCl (pH 7.5), 1 mM EDTA (sodium edetate or ethylenediaminetetraacetic acid, tetrasodium salt) and 10 mM NaCl. This suspension was then briefly sonicated to disrupt the cells to form a cell lysate.

5.8.2 Immunoprecipitation

All subsequent steps were carried out at 4° C. unless otherwise indicated. A 0.5 ul aliquot of mouse monoclonal IgGl antibody (10 mg/ml) against reverse transcriptase from Prague A ASV was added to the lysate and gently mixed for 60 minutes. Subsequently, 2 ul of rabbit anti-mouse antibody (#2177, Dako Accurate, Hicksville, Tenn.) was added to the lysate and gently mixed for 30 minutes. Finally, 100 ul of activated Staphylococcus A protein (Pansorbin, Calbiochem-Behring Corp., La Jolla, Cal.) was added to the lysate and gently mixed for 15 minutes. The Staph A protein was previously activated by repeated washing and centrifugation as follows: Pansorbin was centrifuged at 4000×g for 5 minutes, and resuspended with IP-2 [20 mM Tris-HCl (pH 8.1), 1 mM EDTA, 1% NP-40, 1% deoxycholate, 0.1% SDS and 20 mg/ml bovine serum albumin]. After re-centrifugation the pellet was washed three times with IP-3 (i.e., IP-2 without bovine serum albumin). Finally the pellet was resuspended in an equal volume of IP-1 [20 mM Tris-HCl (pH 8.1), 1 mM EDTA, 1% NP-40].

5.8.3 Preparation for SDS-Page

After the 15 minute incubation with activated Staph A protein, the lysate obtained in Section 5.8.2 was centrifuged at 4000×g for 5 minutes. The resultant pellet was washed once with IP-2, once with IP-2 plus 1M NaCl and three times with IP-3. The final pellet was resuspended in 1 ml IP-1, transferred to a 1.5 ml microcentrifuge tube (Eppendorf tube) and centrifuged (12000×g) for 1 minute. The supernatant was decanted and the final pellet was resuspended in 40 ul of SDS-gel sample buffer [70 mM Tris-HCl (pH 6.8), 5% β-mercaptoethanol, 11.15% glycerine, 0.0015% bromophenol blue and 3% SDS]. After boiling for 2 minutes the sample was re-centrifuged in the Eppendorf microcentrifuge for 2 minutes. The resultant supernatant was removed for analysis by SDS-PAGE (Laemmli, 1970, Nature 227:680).

Using such analysis, the reverse transcriptase protein (90,000 daltons) was found in the extract derived from E. coli transformed with pRT432-1. The corresponding protein was not detected in the control E. coli lysates (i.e., lysates from cells which were not transformed with pRT432-1).

5.9 Purification of the Reverse Transcriptase Gene Product

The isolation of the β-subunit of reverse transcriptase from the transformed bacteria was accomplished using a modification of the methods currently used to isolate the enzyme from virus (Hizi et al., 1977, J. Biol. Chem. 252:2281).

Specifically, 16 g (wet weight) of the E. coli transformants containing the pRT432-1 plasmid were lysed by sonication in buffer containing 20 mM potassium phosphate (pH 7.2), 15 mM β-mercaptoethanol and mM EDTA. Cells were sonicated for two thirty second pulses at 4° C. High molecular weight debris was removed by centrifugation at 20,000×g for 45 min. at 4° C.

Figure 3A:
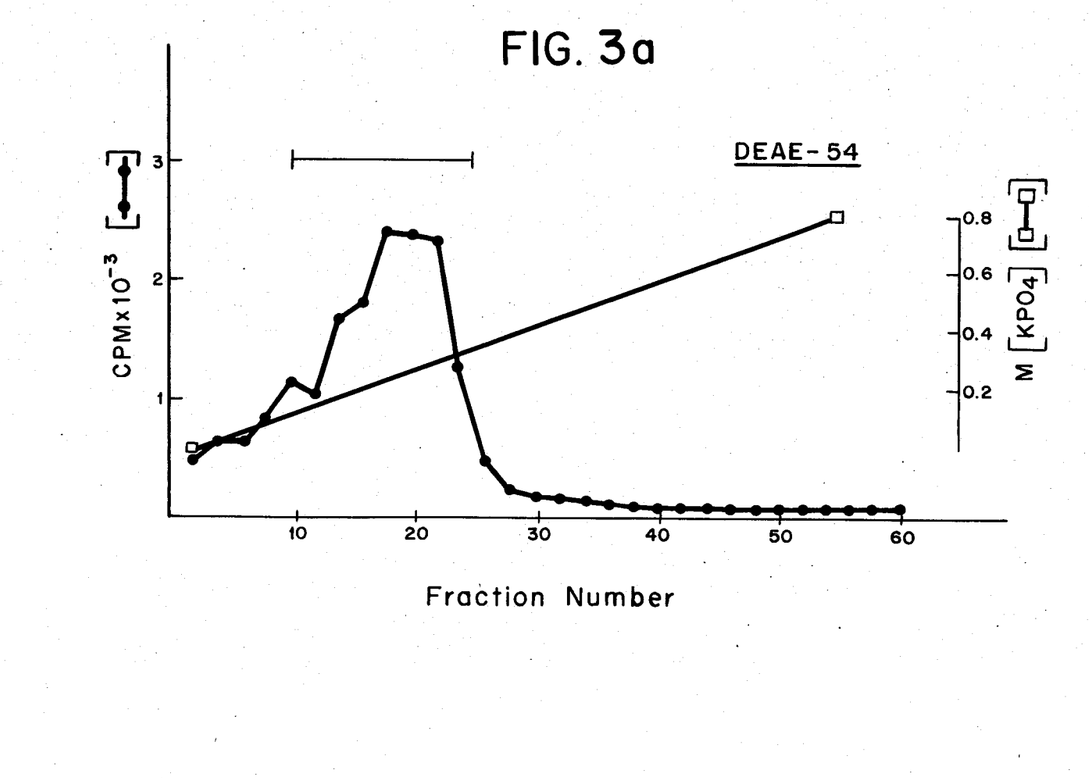
FIG. 3a is a graphic representation of the elution profile, plotted as $CPM \times 10^{-3}$ versus fraction number, of extracts of E. coli transformed with pRT432-1 passed through a DEAE-54 chromatography column.

The supernatant was diluted with four equal volumes of Column Buffer [10 mM potassium phosphate (pH 7.2), 40 mM KCl, 4 mM β-mercaptoethanol, 0.2% NP40 and 10% glycerol]. The diluted E. coli extract was loaded directly on a 0.75 inch by 2 inch DEAE-54 (Whatman) anionic exchange column. The column (after loading) was washed with 50 ml Column Buffer and eluted with an 80 ml linear gradient of 0.01M potassium phosphate (pH 7.2) to 0.6M potassium phosphate (pH 7.2). A total of sixty fractions were collected, each containing 2 ml, and assayed for reverse transcriptase activity using Reaction Buffer consisting of 0.5 mM $MnCl_2$, 50 mM Tris-HCl (pH 8.1), 50 mM KCl, 5 mM dithiothreitol, 8 ug/ml of template Poly(rCm).p(dG)-12-18 (P. L. Biochemicals, Inc., Milwaukee, Wis.) and 20 uCi/ml $^{32}$P-αdGTP (New England Nuclear, Boston, Mass.). Incorporation of $^{32}$P into the oligonucleotides produced is an indication of reverse transcriptase activity (Kieras and Faras, 1975, Virology 65:514). Fractions were assayed by incubating 5 ul of eluant from each fraction with 50 ul each of Reaction Buffer. After 2 hours at 37° C., the samples were precipitated with trichloroacetic acid (TCA) and the precipitates were counted in a scintillation counter. Since the oligonucleotides containing the incorporated $^{32}$P precipitate, an increase in counts per minute (CPM) in the precipitate is an indication of reverse transcriptase activity. The fractions containing reverse transcriptase activity eluted at 0.15 to 0.35 M potassium phosphate (FIG. 3a).

Figure 3B:
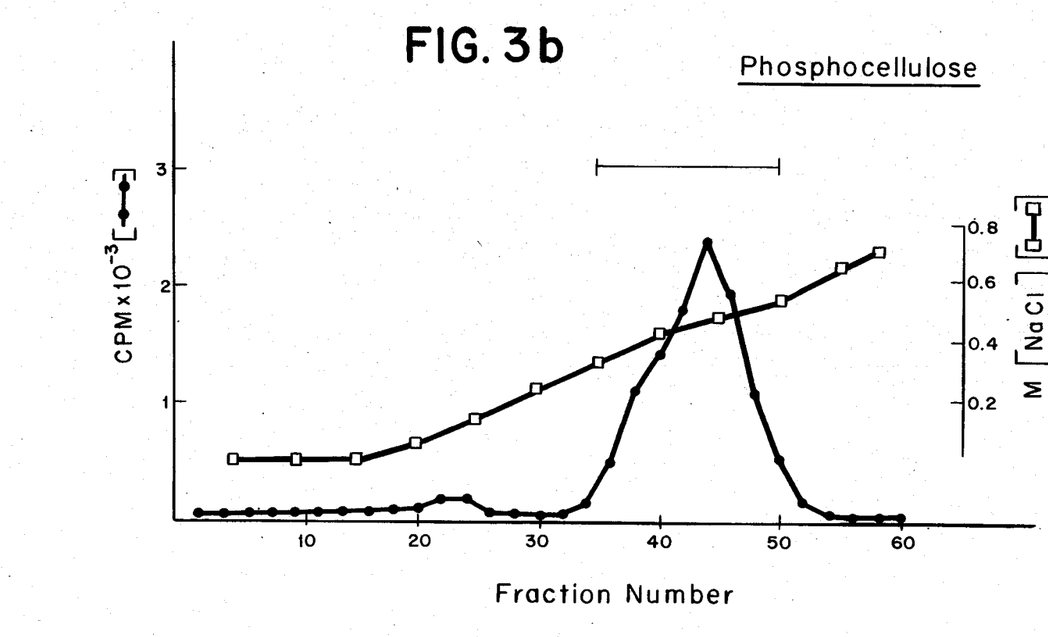

The fractions containing reverse transcriptase activity were pooled, diluted with nine volumes of column buffer and loaded directly onto a 0.5 cm by 20 cm phosphocellulose (P-11, Whatman) anionic exchange column. The column was washed with 50 ml Column Buffer and eluted with a 60 ml linear gradient of 0.01M NaCl to 0.1 M NaCl. Sixty fractions, each containing 1.5 ml, were collected and assayed for reverse transcriptase activity as described above except that KCl was omitted from the Reaction Buffer. Enzyme activity eluted in a single peak between 0.35 and 0.55M NaCl (FIG. 3b).

Figure 3C:
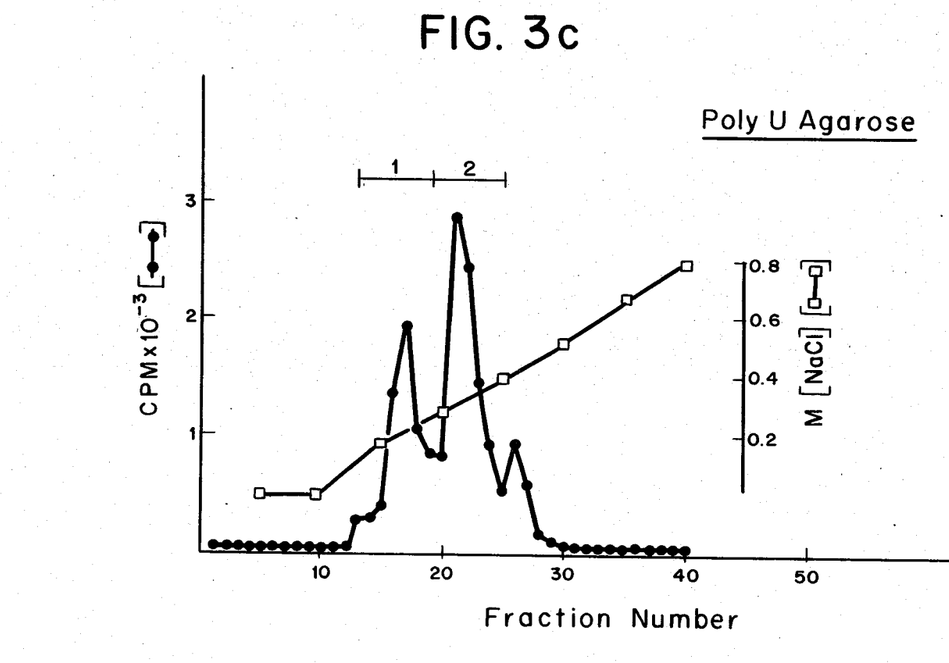
FIG. 3c is a graphic representation of the elution profile from a poly U agarose column, plotted as $CPM \times 10^{-3}$ versus fraction number, of pooled fractions from the chromatography depicted in FIG. 3b.

Those fractions containing reverse transcriptase activity were pooled, diluted with nine volumes of column buffer and loaded on a 5 ml poly U agarose column (P.L. Biochemicals, Inc., Milwaukee, Wis.). The column was washed with 50 ml of Column Buffer and eluted with 2 ml aliquots of 0.1, 0.2, 0.3, 0.4, 0.5, 0.6, 0.7 and 0.8M NaCl in Column Buffer. Forty fractions, 0.5 ml each, were collected and assayed as previously described. Those fractions containing reverse transcriptase activity were resolved in two peaks which eluted between 0.125 and 0.425M NaCl (FIG. 3c). Fractions in each peak were pooled and dialyzed overnight against Column Buffer containing 50% glycerol and stored at −70° C.

An identical purification scheme using an E. coli K12 strain (MC1000) not transformed with pRT432-1 plasmid was performed.

Using such analysis, the reverse transcriptase protein (90,000 daltons) was found in the extracts derived from E. coli transformed with pRT432-1. The corresponding protein was not detected in the control E. coli lysates from cells not transformed with pRT432-1.

5.10 Characterization of the Reverse Transcriptase Gene Product

Reverse transcriptase from the virus (RSV) has a demonstrable preference for certain templates, including primarily RNA templates with DNA primers. The reverse transcriptase isolated from the pooled fractions of peak 1 of the poly U agarose column, Avian Myeloblastosis Virus reverse transcriptase, and E. coli polymerase I, Klenow fragment (New England Biolabs, Inc., Beverly, Mass.) also demonstrate various affinities for various templates, both synthetic and natural. The following reaction buffers were used: Buffer A: 6 mM MgCl$_2$, 40 mM KCl, 50 mM Tris-HCl (pH 8.1), 10 mM β-mercaptoethanol, 10 ug 70S (AMV) RNA, 1 mM dCTP, dATP, dTTP and 20 uCi/ml $^{32}$P-αdGTP; Buffer B: 6 mM MgCl$_2$, 40 mM KCl, 50 mM Tris-HCl (pH 8.1), 10 mM β-mercaptoethanol, 10 ug/ml Poly(rCm)·P(dG)$_{12-18}$ and 20 uCi/ml $^{32}$P-αdGTP; Buffer C: 6 mM MgCl$_2$, 40 mM KCl, 50 mM Tris-HCl (pH 8.1), 10 mM β-mercaptoethanol, 10 ug/ml dC$^m$·dG and 20 uCi/ml $^{32}$P-αdGTP.

Based upon preliminary analysis of polymerase activity (i.e., units/ml of pooled E. coli reverse transcriptase fractions from poly U agarose peak 1, AMV reverse transcriptase, and E. coli polymerase I (Klenow fraction), equal amounts of polymerase activity were incubated in each of the above buffers containing either 70 S RNA, poly(rCm)·p(dG)$_{12-18}$, or dI·dG as template. Reactions were run for 60 minutes at 37° C., then TCA precipitated and the precipatates were counted in a scintillation counter. The results obtained are shown in Table I and Table II. The template preference of the reverse transcriptase produced in E. coli was similar to that of AMV reverse transcriptase. Specifically, both the E coli-produced and AMV reverse transcriptase showed a preference for the natural viral template (70S/RNA) over the synthetic RNA and the snythetic RNA and DNA templates. In contrast, E. coli polymerase I (Klenow), a DNA-dependant DNA polymerase, clearly demonstrated a preference for the DNA template.

TABLE I

Comparison of Template Specificities of Various Polymerases

| Enzyme | Template Used | | |
|---|---|---|---|
|  | 70S RNA | rC$^m$.dG[1] | dC.dG |
| Reverse Transcriptase Produced by E. coli | 3.54[3] | 0.26 | 3.81 |
| Containing the pRT432-1 Plasmid[2] | | | |
| AMV Reverse Transcriptase | 9.08 | 0.97 | 11.5 |
| E. coli Polymerase I (Klenow) | 0.59 | 0.22 | 6.57 |

[1]Poly(rCm).p(dG)12-18.
[2]Pooled fractions of peak 1 of poly U agarose chromatography.
[3]Moles incorporated times 10$^{-14}$.

TABLE II

Comparison of Ratios of Template Specificities of Various Polymerases

| Enzyme | Template Ratio | | |
|---|---|---|---|
|  | 70S RNA/ rC$^m$.dG | 70S RNA/ dC.dG | rC$^m$.dG/ dC.dG |
| Reverse Transcriptase Produced by E. coli containing the pRT432-1 Plasmid[1] | 13.56[2] | 0.93 | 0.07 |
| AMV Reverse Transcriptase | 9.34 | 0.79 | 0.09 |
| E. coli Polymerase I (Klenow) | 2.61 | 0.09 | 0.03 |

[1]Pooled fractions of peak 1 of poly U agarose chromatography.
[2]Ratio of moles incorporated.

It is to be understood that all base pair sizes given for nucleotides are approximate and are used for purposes of description. Furthermore, it is apparent that many modifications and variations of this invention as hereinbefore set forth may be made without departing from the spirit and scope thereof. The specific embodiments described are given by way of example only and the invention is limited only by the appended claims.

We claim:

1. A recombinant plasmid comprising a first DNA sequence derived from an Avian Sarcoma Virus genome and coding for a protein having reverse transcriptase activity, and a second DNA sequence having expression control elements, said recombinant plasmid being capable of replication and directing expression of said DNA sequence in Escherichia coli.

2. The recombinant plasmid of claim 1 further comprising the essential portions of the pBR322 replicon.

3. An Escherichia coli bacterium comprising the recombinant plasmid of claim 1.

4. An Escherichia coli bacterium of claim 3 and as deposited with the ATCC deposit accession No. 31990.

5. A recombinant plasmid of claim 2 designated pRT432-1.

* * * * *